United States Patent [19]
Prince

[11] Patent Number: 5,692,236
[45] Date of Patent: Dec. 2, 1997

[54] WRITING INSTRUMENT FINGER PAD

[76] Inventor: Sandra Prince, 13 St Walburges Gardens, Ashton on Ribble, England, PRZ ZQJ

[21] Appl. No.: 554,442

[22] Filed: Nov. 8, 1995

[51] Int. Cl.$^6$ .................................................. A41D 13/00
[52] U.S. Cl. .................................................................. 2/21
[58] Field of Search .................................. 2/21, 163, 16, 2/22, 908, 910, 911, 164, 161.6; 602/22, 41, 61, 62

[56] References Cited

U.S. PATENT DOCUMENTS

| | | |
|---|---|---|
| 1,359,717 | 11/1920 | McCarthy ............................ 2/21 X |
| 1,555,960 | 10/1925 | Fuller .................................. 2/21 X |
| 1,863,960 | 6/1932 | Aronson ............................... 2/21 |
| 2,740,121 | 4/1956 | Seidel .................................. 2/21 |
| 4,194,736 | 3/1980 | Loafman ............................. 2/21 X |
| 4,257,596 | 3/1981 | Capella ............................... 2/21 X |
| 4,615,046 | 10/1986 | Martin ................................. 2/21 |
| 5,517,692 | 5/1996 | Wunderlich-Kehm ............... 2/21 |

*Primary Examiner*—Paul C. Lewis

[57] ABSTRACT

A pad for protecting an engaging finger utilized with a writing instrument. The inventive device includes a cover web extendable at least partially about a digit of a human hand. A securing assembly is coupled to the web for securing a web in an annular configuration about the digit to secure the device thereto.

1 Claim, 4 Drawing Sheets

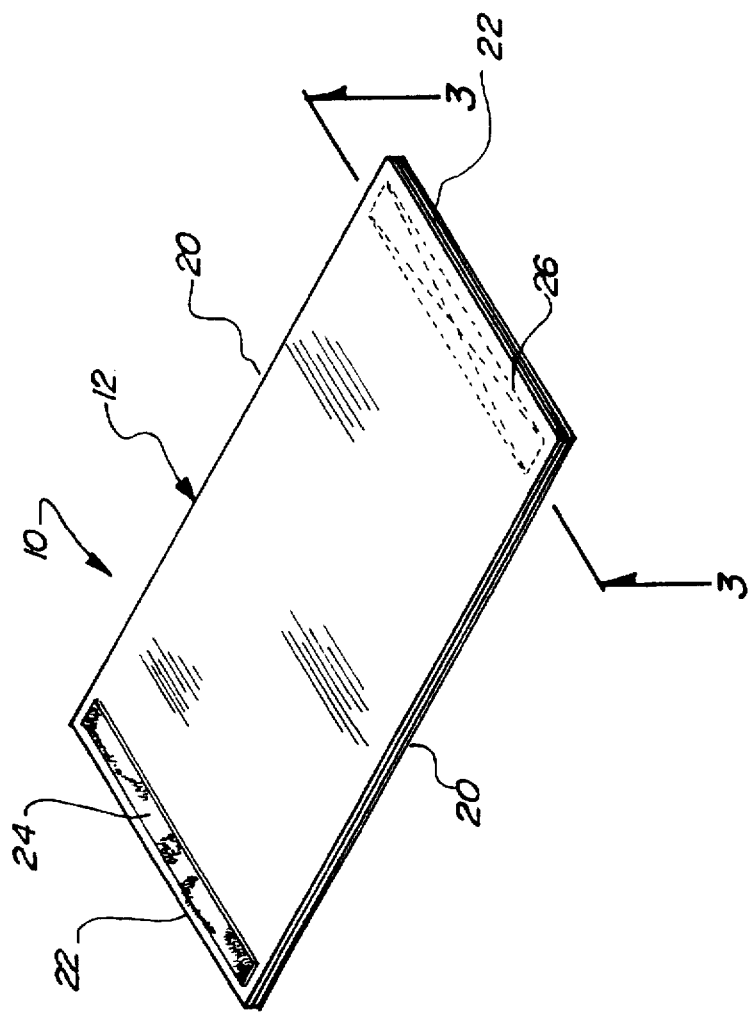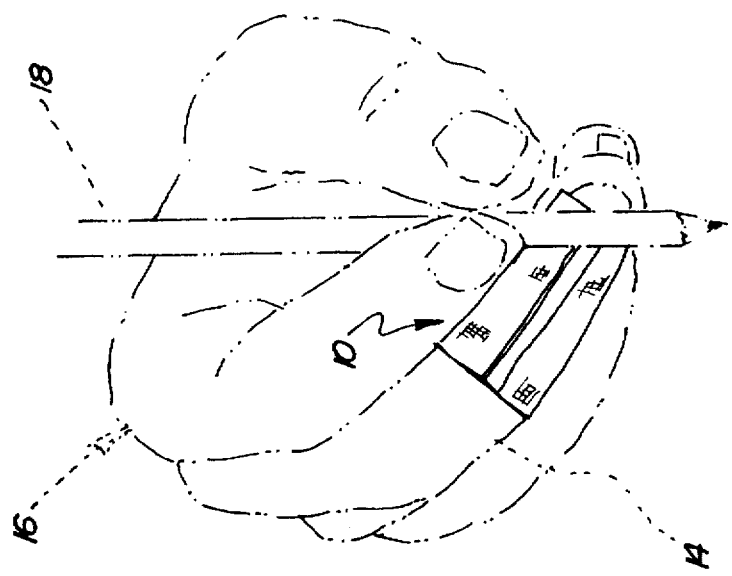

Fig. 7
Fig. 8
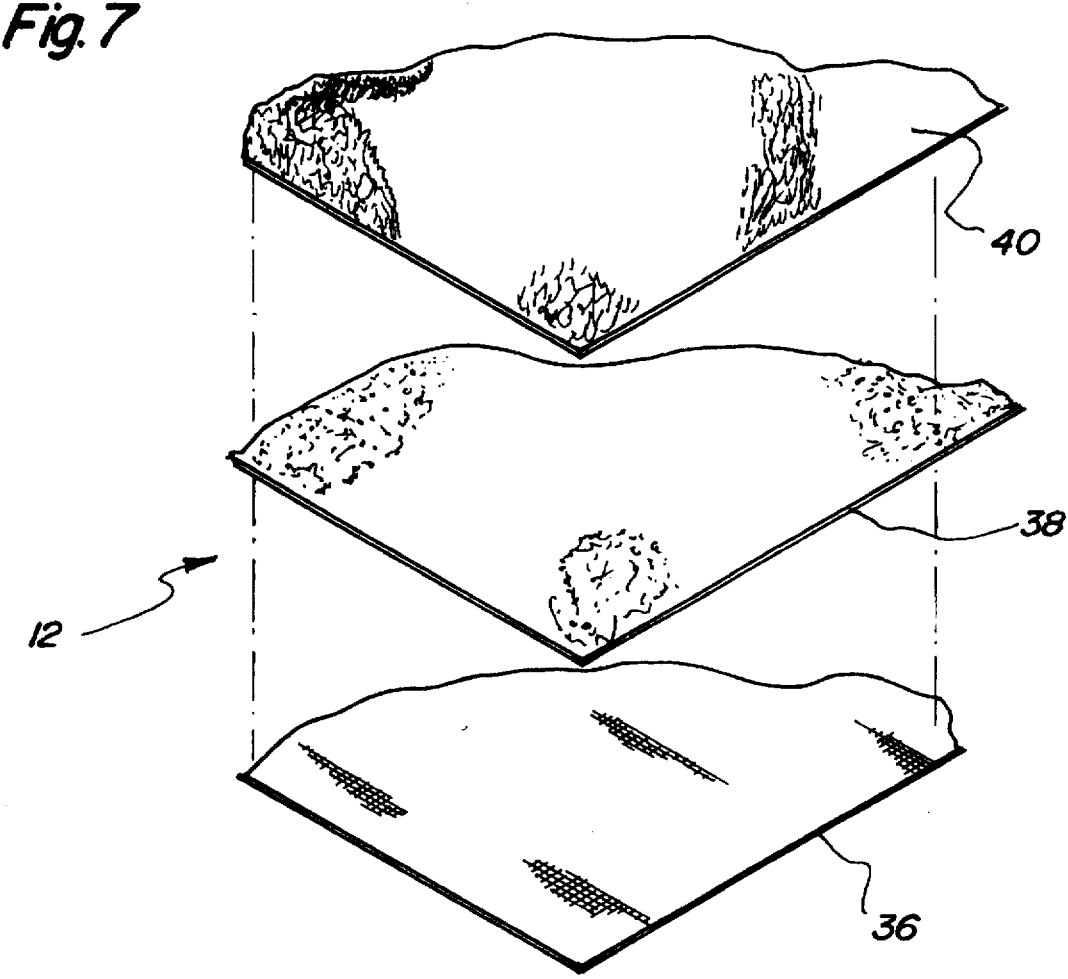
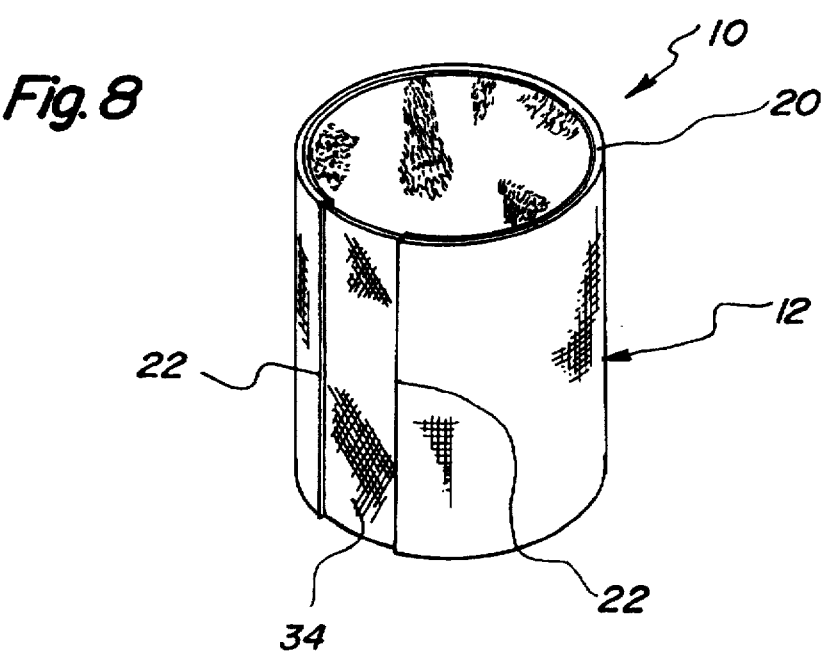

WRITING INSTRUMENT FINGER PAD

BACKGROUND OF THE INVENTION

1. Field of the Invention

The present invention relates to writing instrument gripping devices and more particularly pertains to a writing instrument finger pad for protecting an engaging finger utilized with a writing instrument.

2. Description of the Prior Art

The use of writing instrument gripping devices is known in the prior art. More specifically, writing instrument gripping devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art writing instrument gripping devices include U.S. Pat. No. 5,056,945; U.S. Pat. No. 5,143,463; U.S. Pat. No. 5,180,239; U.S. Pat. No. 3,721,006; U.S. Design Pat. No. 318,295; and U.S. Design Pat. No. 342,968.

While these devices fulfill their respective, particular objectives and requirements, the aforementioned patents do not disclose a writing instrument finger pad for protecting an engaging finger utilized with a writing instrument which includes a cover web extendable at least partially about a digit of a human hand, and a securing assembly coupled to the web for securing the web in an annular configuration about the digit to secure the device thereto.

In these respects, the writing instrument finger pad according to the present invention substantially departs from the conventional concepts and designs of the prior art, and in so doing provides an apparatus primarily developed for the purpose of protecting an engaging finger utilized with a writing instrument.

SUMMARY OF THE INVENTION

In view of the foregoing disadvantages inherent in the known types of writing instrument gripping devices now present in the prior art, the present invention provides a new writing instrument finger pad construction wherein the same can be utilized for protecting an engaging finger utilized with a writing instrument. As such, the general purpose of the present invention, which will be described subsequently in greater detail, is to provide a new writing instrument finger pad apparatus and method which has many of the advantages of the writing instrument gripping devices mentioned heretofore and many novel features that result in a writing instrument finger pad which is not anticipated, rendered obvious, suggested, or even implied by any of the prior art writing instrument gripping devices, either alone or in any combination thereof.

To attain this, the present invention generally comprises a pad for protecting an engaging finger utilized with a writing instrument. The inventive device includes a cover web extendable at least partially about a digit of a human hand. A securing assembly is coupled to the web for securing a web in an annular configuration about the digit to secure the device thereto.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carded out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new writing instrument finger pad apparatus and method which has many of the advantages of the writing instrument gripping devices mentioned heretofore and many novel features that result in a writing instrument finger pad which is not anticipated, rendered obvious, suggested, or even implied by any of the prior art tool guides, either alone or in any combination thereof.

It is another object of the present invention to provide a new writing instrument finger pad which may be easily and efficiently manufactured and marketed.

It is a further object of the present invention to provide a new writing instrument finger pad which is of a durable and reliable construction.

An even further object of the present invention is to provide a new writing instrument finger pad which is susceptible of a low cost of manufacture with regard to both materials and labor, and which accordingly is then susceptible of low prices of sale to the consuming public, thereby making such writing instrument finger pads economically available to the buying public.

Still yet another object of the present invention is to provide a new writing instrument finger pad which provides in the apparatuses and methods of the prior art some of the advantages thereof, while simultaneously overcoming some of the disadvantages normally associated therewith.

Still another object of the present invention is to provide a new writing instrument finger pad for protecting an engaging finger utilized with a writing instrument.

Yet another object of the present invention is to provide a new writing instrument finger pad which includes a cover web extendable at least partially about a digit of a human hand, and a securing assembly coupled to the web for securing the web in an annular configuration about the digit to secure the device thereto.

These together with other objects of the invention, along with the various features of novelty which characterize the invention, are pointed out with particularity in the claims annexed to and forming a pan of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a writing instrument finger pad according to the present invention in use.

FIG. 2 is an isometric illustration of the invention, per se.

FIG. 7 is an exploded isometric illustration of a portion of the cover web.

FIG. 8 is an isometric illustration of the invention including a further alternative form of the securing means.

DESCRIPTION OF THE PREFERRED EMBODIMENT

Figure 3:
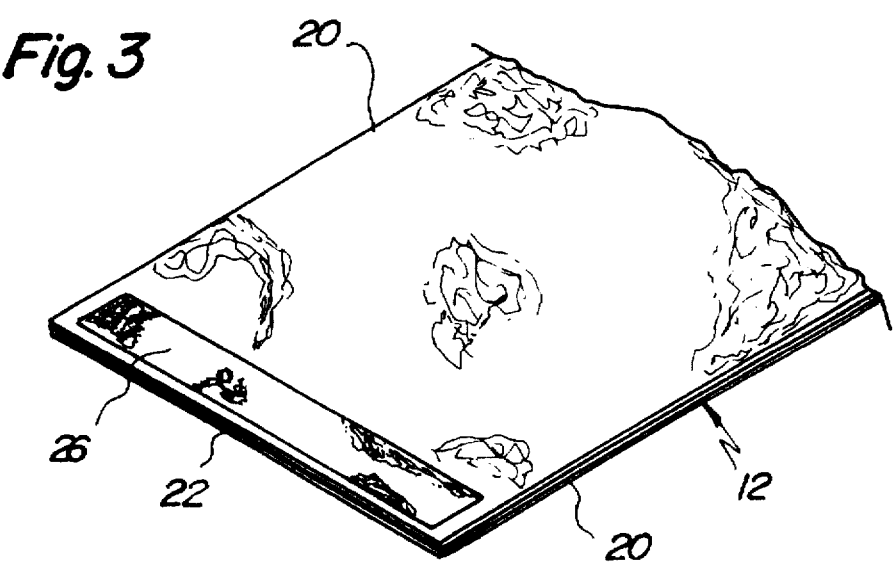
FIG. 3 is a bottom isometric illustration of a portion of the invention taken from line 3—3 of FIG. 1.

With reference now to the drawings, and in particular to FIGS. 1-8 thereof, a new writing instrument finger pad embodying the principles and concepts of the present invention and generally designated by the reference numeral 10 will be described.

More specifically, it will be noted that the writing instrument finger pad 10 comprises a composite cover web 12 which can be extended at least partially about a digit 14 of a human hand 16 substantially as shown in FIG. 1 of the drawings. An unlabeled securing means is coupled to the composite cover web 12 for securing the cover web in an angular configuration about the digit of the human hand 16 so as to secure the device 10 relative thereto. By this structure, the particular digit 14 of the human hand 16 to which the device 10 is attached is protected from abrasive engagement with a writing instrument 18 utilized during a writing procedure substantially as shown in FIG. 1 of the drawings.

Referring now to FIGS. 2 and 3 wherein the present invention 10 is illustrated in detail, it can be shown that the composite cover web 12 is shaped so as to define substantially spaced and parallel linear longitudinal edges 20, with linear transverse edges 22 extending substantially orthogonally between respectively opposed ends of the linear longitudinal edges 20 so as to define a substantially rectangular shape of the composite cover web 12 as shown in FIGS. 2 and 3 of the drawings. By this structure, the composite cover web 12 can be wrapped about the digit 14 of a human hand 16 such that a first one of the linear transverse edges 22 overlap a second one of the linear transverse edges 22.

With continuing reference to FIGS. 2 and 3, it can be shown that the securing means of the present invention 10 preferably comprises a first patch 24 of hook and loop fabric fastening material such is commonly known under the trademark named "VELCRO" secured to an upper surface of the composite cover web 12 proximal to a first one of the linear transverse edges 22 thereof. Similarly, a second patch 26 of hook and loop fabric fastening material is secured to a lower surface of the composite cover web 12 proximal to a second one of the linear transverse edges 22 thereof. By this structure, the first patch 24 of hook and loop fabric fastening material can be cooperatively engaged with the second patch 26 of hook and loop fabric fastening material so as to couple the cover web 12 about the digit 14 of the human hand 16 as shown in FIG. 1 of the drawings.

Figure 4:
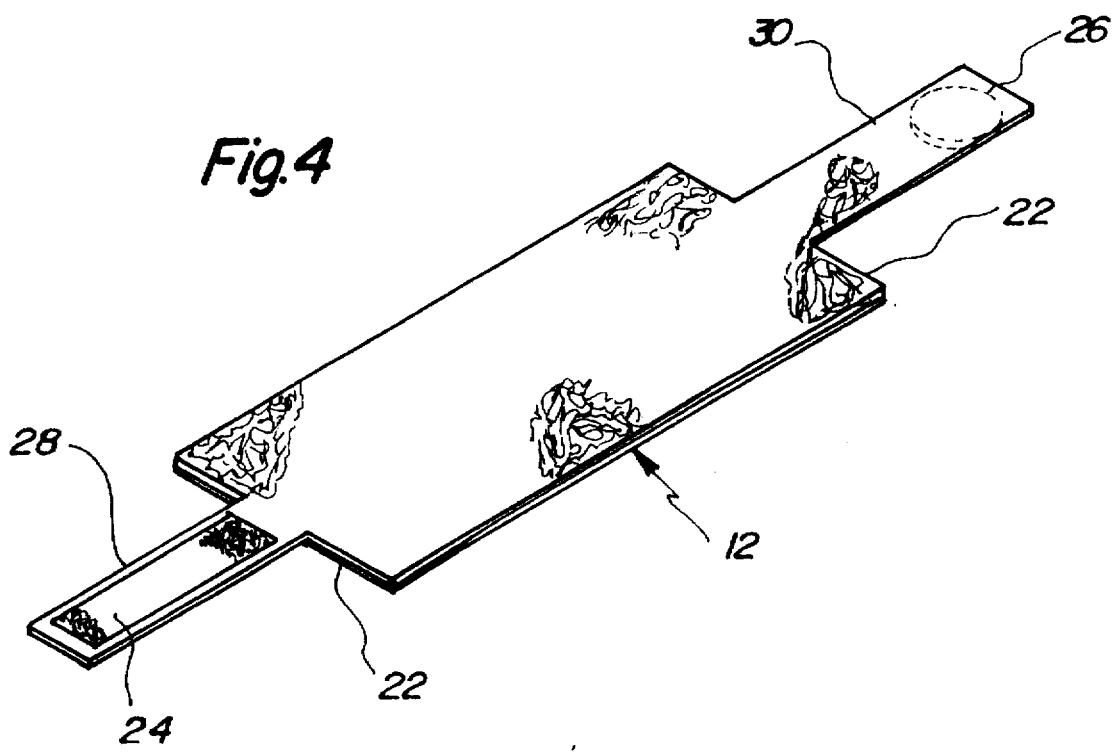
FIG. 4 is an isometric illustration of an alternative form of a securing means comprising a portion of the present invention.

Referring now to FIG. 4, it can be shown that the securing means of the present invention 10 may alternatively comprise a first strap 28 extending from a first one of the transverse edges 22 of the composite cover web 12 and having the first patch 24 of hook and loop fabric fastening material coupled thereto. A second strap 30 extends from a second one of the transverse edge 22 of the cover web 12 and includes the second patch 26 of hook and loop fabric fastening fabric material coupled thereto. By this structure, and in a manner similar to that of the securing means illustrated in FIGS. 2 and 3, the patches 24 and 26 of hook and loop fabric fastening material coupled to the respective straps 28 and 30 can be cooperatively engaged together so as to mount the cover web 12 about the digit 14 of the human hand 16.

Figure 5:
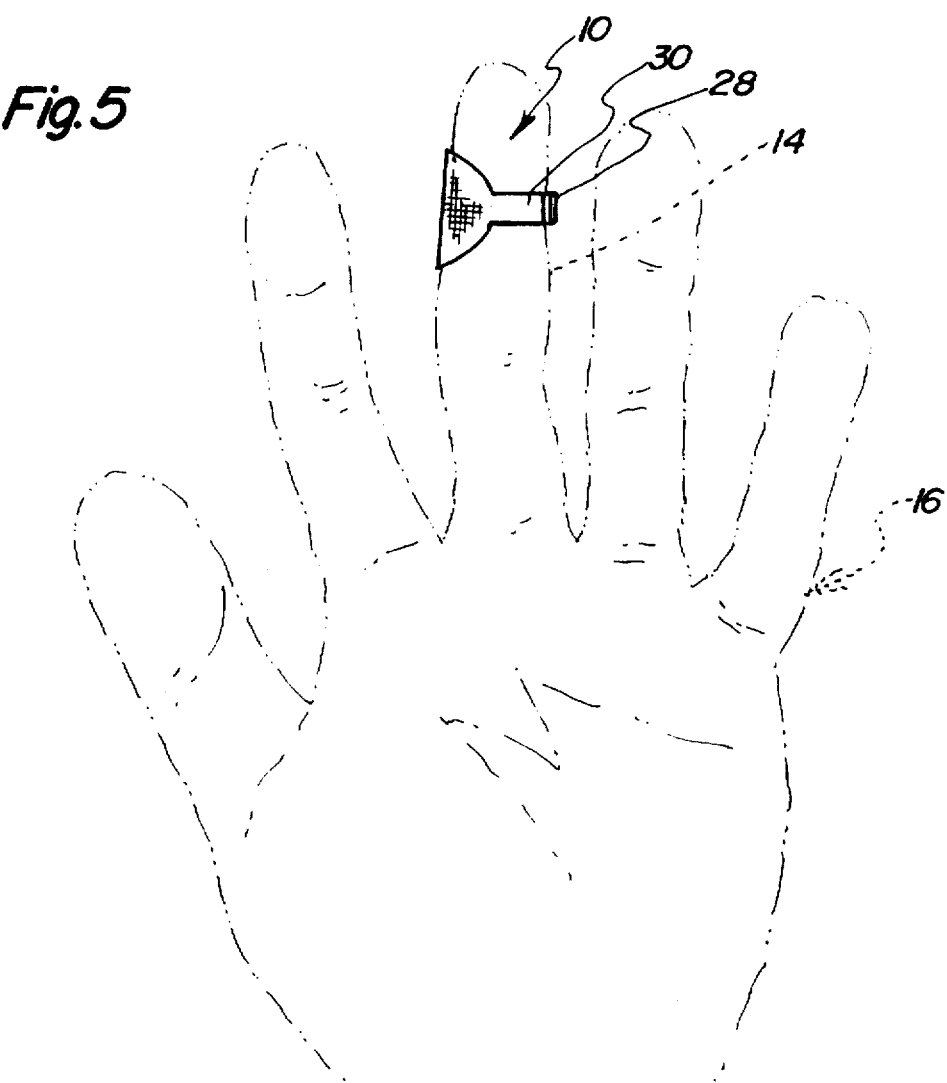
FIG. 5 is an isometric illustration of the invention in use including the alternative form of the securing means and an alternative form of the cover web of the invention.
Figure 6:
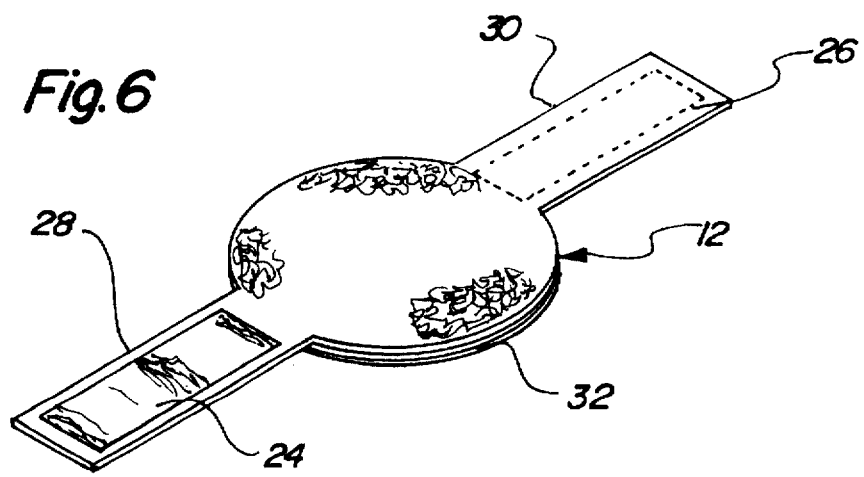
FIG. 6 is an isometric illustration of the invention as shown in FIG. 5, per se.

As shown in FIGS. 5 and 6, the composite cover web 12, in lieu of the rectangular shaped illustrated in FIGS. 1 through 4, may be shaped so as to define a circular outer peripheral edge 32 with the straps 28 and 30 projecting from diametrically opposed sides of the composite cover web 12 and operating as described above in conjunction with FIG. 4 of the drawings. By this structure, the circular outer peripheral edge 32 of the composite cover web 12 engages less of the palm side of the digit 14 relative to the rectangular form of the cover web 12 illustrating FIGS. 1 through 4 of the drawing so as to permit for ease of articulation of the outer tip of the digit 14 of the human hand 16 to which the device 10 is attached.

Referring now to FIG. 8, it can be shown that the securing means, in lieu of the patches 24 and 26 of the hook and loop fabric fastening material, may further alternatively comprise an elastic band 34 coupled to and extending between the transverse edges 22 of the cover web 12 so as to retain the cover web 12 in a normally angular configuration. By this structure, the elastic band 34 can be selectively deformed or elongated during insertion of the digit 14 of the human hand 16 thereinto, whereby a resilient contraction of the elastic band 34 will result in a frictional engagement of an interior surface of the cover web 12 with an exterior surface of the digit 14 of the human hand 16 so as to retain the device 10 relative thereto.

Referring now to FIG. 7, it can be shown that the cover web 12 may be comprised of a plurality of fabric webs coupled together so as to provide a desired feel, texture, and engaging surface relative to the device 10. To this end, the cover web 12 preferably comprises a fabric mesh web 36, with a padded web 38 coupled to and coextensively covering the fabric mesh web 36. A soft cloth web 40 is coupled to and coextensively covers the padded web 38, with the fabric mesh web 36 defining an exterior of the device 10 in use, and the soft cloth web 40 defining an interior surface of the cover web in use. By this structure, the soft cloth web 40 comfortably engages human skin of the digit 14 of the human hand 16, the fabric mesh web 36 securely engages an exterior surface of the writing instrument 18 when held as shown in FIG. 1 of the drawings, and the padded web 38 providing a degree of padding between the writing instrument 18 and the digit 14 of the human hand 16 so as to reduce fatigue and/or irritation thereto.

In use, the writing instrument finger pad 10 of the present invention can be easily utilized for protecting an engaging FIG. 14 of a human hand 16 during use of a writing instrument 18. The various forms of the securing means of the present invention 10 allows the device 10 to be constructed in an adjustable manner as shown in FIGS. 1 through 6, or alternatively in a fitted manner as shown in FIG. 1 of the drawing. The various shapes of the composite cover web 12 allow the present invention 10 to be utilized in the coveting of a digit 14 which need not be articulated, or alternatively in the coveting of a digit in which articulation thereof is needed.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A writing instrument finger pad comprising:

a composite cover web extendable at least partially about a digit of a human hand;

wherein the cover web comprises of a plurality of fabric webs coupled together, wherein the cover web comprises a fabric mesh web; a padded web coupled to and coextensively covering the fabric mesh web; and a soft cloth web coupled to and coextensively covering the padded web such that the fabric mesh web defines an exterior surface of the cover web, and the soft cloth web defines an interior surface of the cover web whereby the soft cloth web comfortably engages human skin of the digit of the human hand, the fabric mesh web securely engages an exterior surface of the writing instrument when held, and the padded web provides a degree of padding between the writing instrument and the digit of the human hand to reduce fatigue and irritation;

a securing means coupled to the cover web for securing the cover web in an angular configuration about a digit of a human hand so as to secure the pad relative thereto;

said cover web shaped so as to define substantially spaced and parallel linear longitudinal edges, with linear transverse edges extending substantially orthogonally between respectively opposed ends of the linear longitudinal edges so as to define a substantially rectangular shape of the cover web, with the cover web being adapted for wrapping about a digit of a human hand such that a first one of the linear transverse edges overlaps a second the of the linear transverse edges;

wherein the securing means comprises a first patch of hook and loop fabric fastening material secured to an upper surface of the composite cover web proximal to the first one of the linear transverse edges thereof; and a second patch of hook and loop fabric fastening material secured to a lower surface of the composite cover web proximal to the second one of the linear transverse edges thereof, whereby the first patch of hook and loop fabric fastening material can be cooperatively engaged with the second patch of hook and loop fastening material so as to couple the cover web about the digit of the human hand.

* * * * *